United States Patent [19]
Kuo et al.

[11] Patent Number: 5,856,352
[45] Date of Patent: *Jan. 5, 1999

[54] ABRUQUINONE DERIVATIVES USEFUL IN THE TREATMENT OF INFLAMMATION AND ALLERGIC REACTIONS

[75] Inventors: Sheng-Chu Kuo; Sheng-Chih Chen; Jin-Bin Wu; Che-Hing Teng; Jih-Pyang Wang, all of Taichung, Taiwan

[73] Assignee: National Science Council, Taipei, Taiwan

[ * ] Notice: The term of this patent shall not extend beyond the expiration date of Pat. No. 5,563,167.

[21] Appl. No.: 841,729

[22] Filed: Apr. 29, 1997

[51] Int. Cl.$^6$ ...................................................... A61K 31/35
[52] U.S. Cl. ............................................................. 514/456
[58] Field of Search ............................................... 514/456

[56] References Cited

U.S. PATENT DOCUMENTS 5,563,167  10/1996  Kuo et al. ................................ 514/451

OTHER PUBLICATIONS

Kuo et al, Chemical Abstracts, vol. 123, abstract No. 218351, 1995.

Wang et al, Chemical Abstracts, vol. 122, abstract No. 96065, 1995.

*Primary Examiner*—William R. A. Jarvis
*Attorney, Agent, or Firm*—W. Wayne Liauh

[57] ABSTRACT

Disclosed are methods of providing antiinflammatory activity and inhibiting allergic reaction by administering Abruquinones A, B, D, E, or F to a subject in need thereof.

12 Claims, No Drawings

ABRUQUINONE DERIVATIVES USEFUL IN THE TREATMENT OF INFLAMMATION AND ALLERGIC REACTIONS

The present invention relates to the preparation, isolation, and the therapeutical applications of several novel natural isoflavanquinone derivatives. These isoflavanquinone derivatives are Abruquinones A, B, D, E, and F, which are shown as Compounds I through V, respectively, as follows:

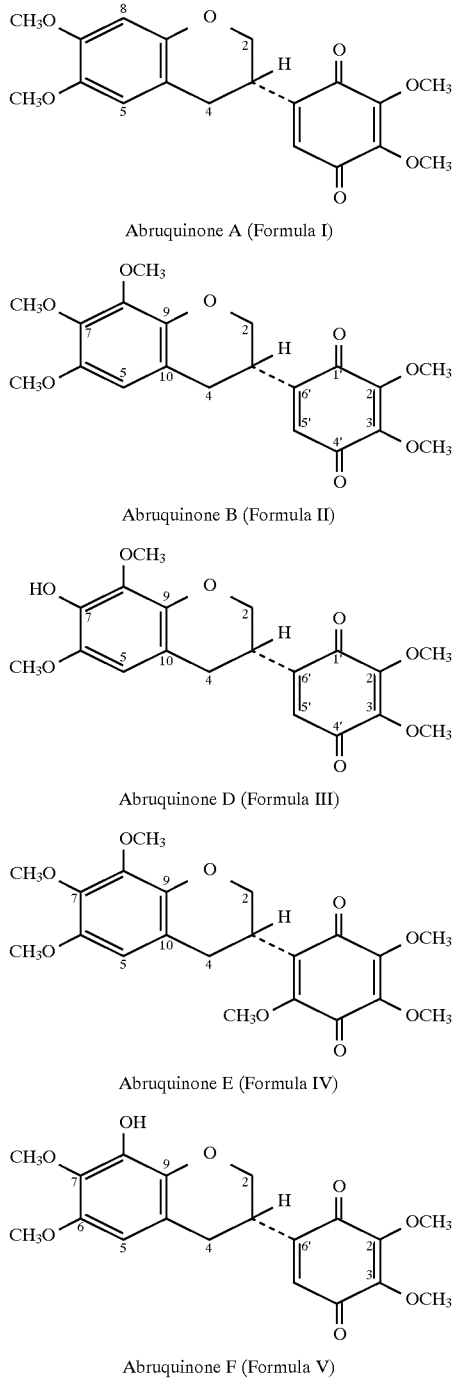

Abruquinone A (Formula I)

Abruquinone B (Formula II)

Abruquinone D (Formula III)

Abruquinone E (Formula IV)

Abruquinone F (Formula V)

BACKGROUND OF THE INVENTION

Hsiang-ssu-tzu (*Abrus precatorius* L.), a medical plant of leguminosae, was described for the first time in the ancient Chinese medicine book, "Pen-Tsao-Kan-Mu" (Shin-Chen, Li; 1518–1593), by its therapeutical use in folk medicine:

Cardiovascular diseases, especially the various forms of thrombosis, such as coronary, embolic, venous, and traumatic thrombosis, account for a large number of deaths per year. In fact, it is estimated by the American Heart Association that 54% of all deaths in the United States are attributed to cardiovascular disease. It is therefore important for us to be familiar with the physical, chemical, and clinical aspects of drugs used to treat these forms of thrombosis. Since it is believed that initiation of thrombus formation is dependent of platelet aggregation, inhibitors of platelet aggregation may be prototypes of drugs that can effectively combat thrombosis, which leads to heart attacks and stokes. It has prompted us to search for novel compounds possessing more potent inhibitive activity on platelet aggregation.

On the other hand, rheumatic diseases are classified as chronic connective tissue diseases and belong to the complex group of active immunity inflammatory conditions. They may disable single or multiple organ systems of the body and affect approximately 20 million Americans. Therapy is not directed primarily to the inflammatory processes. The development of antiinflammatory drugs started with the use of salicylates at the end of the nineteenth century. Interest in the pyrazolones resulted in the discovery of phenylbutazone. The 1950's was the decade of the corticosteroids; this was followed by an effort to find potent non-steroidal substances that do not have the side effects of corticosteroids, which were culminated in the 1960's with indomethacin. More recently, many laboratories are engaged in the synthesis and evaluation of compounds belonging to different chemical classes. However, few attention is paid to plant constituents which may possess immunosuppressive nature. The present invention discloses the potent antiinflammatory property of the novel abruquinone derivatives determined by measuring the inhibitory activity on the release of B-glucuronidase, lysozyme, and superoxide from neutrophils induced by FMLP.

Similar evaluation, which was carried out by measuring the inhibitory activity of the novel abruquinone derivatives on the release of B-glucuronidase and histamine from mast cells using compound 48/80 as an inducer, also revealed their antiallergic property. Hypersensitivity or allergic reactions cause many chronic and acute illnesses, including hay fever, pruritus, contact dermatitis, drug rashes, urticaria, atopic dermatitis, and analphylactic shock. In fact, about 1 in 10 Americans have allergy. Desensitization is the most common treatment for allergy. The procedure is undertaken to prevent antigen-antibody reactions and thus stop the release of chemical mediators. This led the allergists to attempt to build up the patient's immunity to the antigen. Thus, many natural products and synthetic compounds were investigated. The isolation of khellin (VI) led to the finding of cromolyn sodium (VII). However, cromolyn sodium is poorly absorbed orally and thus is administered in the form of a powder aerosol. This drug is prophylactic and does not inhibit the action of histamine, SRS-A, or any other phylactic chemical mediators. So far, the experimental results show that the potency of compounds disclosed in this invention are superior than indomethacin (Compound VI) and cromolyn sodium (Compound VII) in antiinflammatory and antiallergic evaluations. Compounds VI and VII are shown below:

The investigation of the contents of Hsiang-ssu-tzu (*Abrus precatorius* L.) was performed in some laboratories (Khaleque, A. et al., Sci. Res. 3, 203, 1996; Ghosal, S. et al., Phytochemistry, 10, 159, 1971; Chiang, T. C. et al., J. Chem. Soc. Chem. Comm., 20, 1197, 1982; Planta medica 49, 165, 1983). Abruquinone A, B, C were isolated for the first time from the roots of this plant by Lupi, A. et al., (Gazz. Chim.

Ital., 109, 9, 1979). These authors have tried to synthesize Abruquinones A and B (Lupi, A. et al., Gazz. Chim. Ital., 110, 625, 1980). As to their biological activity, only one paper has described the inhibitory activity of Abruquinone A on the growth of *Trypanosoma cruz* and *Crithidia fasciculata* (Goijman, S. G. et al., Experientia, 41, 646, 1985).

DETAILED DESCRIPTION

The present invention discloses the efficient methods of isolation and purification of the active constituents from the root and stem parts of the medicinal plant, *Abrus precatorius* L. and the platelet aggregation inhibitory activity, as well as the antiinflammatory and antiallergic activities of these constituents.

1. Isolation and Purification:

The root and stem parts of *Abrus precatoreius* L. were extracted with a polar organic solvent such as methanol, ethanol, and acetone. Solvent of the extract was evaporated and the residue was suspended in water and extracted with chloroform or other non-polar organic solvents. The chloroform extract was then purified through silica gel column, and Abruquinones A, B, D, E, and F (I–V) were obtained. Compounds III–V were found for the first time in this invention. Structures of these compounds were elucidated on the basis of their IR, UV, $^1$H-NMR, $^{13}$C-NMR Mass spectra as well as elemental analytical data.

II. Pharmacological activity:

(1) Inhibiting activity on platelet aggregation

A. Preparation of aggregation inducing agent

1. Thrombin (bovine) was dissolved in 50% glycerol to give a stock solution of 100 NIH unit/ml.

2. Collagen (bovine tendon) in 25 mM aqueous acetic acid was grounded at 4° C. to form a well dispersed suspension (1 mg/ml) and store at −70° C. Before using, it was thawed and well grounded and diluted to 10 $\mu$g/ml.

3. PAF was dissolved in $CCl_4$ and stocked at 20° C. Before using, it was diluted with deionized water.

4. Arachidonic acid (AA) was dissolved in deionized water to give a solution of 100 M.

B. Preparation of platelets

The suspension of platelets were prepared according to the reported method. The blood from the vein of a rabbit's ear and 100 mM of EDTA were mixed in the ratio of 1:14 (V/V) and immediately separated by centrifuge (90 X g) at room temperature for 10 minutes. The enriched platelets in the upper plasma layer were subjected to centrifuge (500 X g) for 10 minutes. After the plasma was removed, the platelets in the lower layer were suspended in Tyrode solution containing EDTA (2 mM) and bovine serum albumin (3.5 mg/ml), and then subjected to centrifuge (500 X g) again for 10 minutes. The platelets so obtained were suspended in a Tyrode solution containing no EDTA, and was adjusted to about 4.5×10$^8$ cell/ml by a counter. One mM of calcium ion ($CA^{2+}$) was added to the suspension. Thirty minutes after the addition, the experiment was conducted. The composition of the Tyrode's solution (mM) was: NaCl (136.9), KCl (2.8), $NaH_2PO_3$ (0.33), $NaHCO_3$ (11.9), glucose (11.2) and $MgCl_2$ (1.1).

C. Platelet aggregation and ATP release reaction test

The method reported by Born, G.V.R. (J. Physiol. 168, 178, 1963) was used to determine platelet aggregation, in which a Lumi-aggregometer (Model 1020, Payton, Canada) was used. Platelet suspension (0.4 ml) was added into a small glass tube coated with silicone, and stirred at 900 rpm with a small magnetic stirrer. Unless otherwise specified, the antagonist was added 1 minute before the inducing agent, and all the reactions were carried out at 37° C.

The aggregation was calculated by the following formula:

$$\text{aggregation } (\%) = \frac{A_1 - A_2}{5} \times 100\%$$

$A_1 - A_b$ $A_1$=tramsmittance before inducing.

$A_2$=transmittance after inducing.

$A_b$=transmittance of Tyrode solution.

Tabs. 1–5 show the significant inhibitory activities of compounds I–V at the dose level 2–100 $\mu$g/ml with respect to the platelet aggregations induced by thrombin, arachidonic acid (AA), collagen, and PAF.

TABLE 1

| Abruquinone A (I) Aggregation % | | | | |
|---|---|---|---|---|
| ($\mu$g/ml) | thrombin | AA | collagen | PAF |
| control | 94.3 ± 0.3 | 91.5 ± 2.1 | 95.3 ± 1.7 | 92.5 ± 2.6 |
| 100 | 0*** | — | — | — |
| 50 | 6.9 ± 6.3*** | — | — | — |
| 20 | 9.5 ± 8.7*** | — | — | 0*** |
| 10 | 70.5 ± 10.8* | 0*** | 0*** | 14.0 ± 12.8*** |
| 5 | 98.5 ± 0.9 | 7.7 ± 7.2*** | 30.7 ± 14.0*** | 79.7 ± 5.3* |
| 2 | — | 35.0 ± 15.3** | 85.9 ± 5.2 | 92.8 ± 1.9 |

1. % Aggregation (Mean ± S.E. (n)) n = 3
2. Thrombin: 0.1 u/ml, AA: 100 $\mu$M, collagan: 100 $\mu$g/ml, PAF: 2 ng/ml
3. *p < 0.05; p < 0.01; *p < 0.001

TABLE 2

| Abruquinone B (II) Aggregation % | | | | |
|---|---|---|---|---|
| ($\mu$g/ml) | thrombin | AA | collagen | PAF |
| control | 92.4 ± 0.9 | 84.6 ± 0.8 | 88.6 ± 0.7 | 91.8 ± 1.6 |
| 20 | 0.0 ± 0.0*** | 0.0 ± 0.0*** | 0.0 ± 0.0*** | 0.0 ± 0.0*** |
| 10 | 10.5 ± 8.6*** | 0.0 ± 0.0*** | 0.0 ± 0.0*** | 6.8 ± 5.6*** |
| 5 | 85.2 ± 0.6*** | 5.1 ± 4.2*** | 9.7 ± 7.9*** | 75.3 ± 2.7*** |
| 2 | 91.2 ± 0.4 | 72.4 ± 3.4** | 77.5 ± 0.7*** | — |
| 1 | — | 81.1 ± 0.2** | 83.3 ± 1.1*** | — |

1. % Aggregation (Mean ± S.E. (n)) n = 3
2. Thrombin: 0.1 u/ml, AA: 100 $\mu$M, collagan: 100 $\mu$g/ml, PAF: 2 ng/ml
3. *p < 0.05; p < 0.01; *p < 0.001

TABLE 3

| Abruquinone D (III) Aggregation % | | | | |
|---|---|---|---|---|
| ($\mu$g/ml) | thrombin | AA | collagen | PAF |
| control | 91.0 ± 0.7 | 91.5 ± 1.8 | 89.3 ± 1.8 | 90.2 ± 1.6 |
| 100 | 3.7 ± 3.0*** | 0.0 ± 0.0*** | 17.9 ± 10.3*** | 9.7 ± 8.0 |
| 50 | 22.1 ± 1.6*** | 0.0 ± 0.0*** | — | 23.3 ± 2.7*** |
| 20 | 33.8 ± 3.3*** | 0.0 ± 0.0*** | — | 30.2 ± 1.5*** |
| 10 | 85.1 ± 0.7** | 26.7 ± 11.6*** | — | 69.5 ± 6.0** |
| 5 | — | 72.1 ± 6.8 | — | 88.3 ± 0.7 |
| 2 | — | 88.1 ± 2.2 | — | — |

1. % Aggregation (Mean ± S.E. (n)) n = 3
2. Thrombin: 0.1 u/ml, AA: 100 $\mu$M, collagan: 100 $\mu$g/ml, PAF: 2 ng/ml
3. *p < 0.05; p < 0.01; *p < 0.001

TABLE 4

Abruquinone E (IV) Aggregation %

| (μg/ml) | thrombin | AA | collagen | PAF |
|---|---|---|---|---|
| control | 92.4 ± 0.9 | 84.6 ± 0.8 | 88.6 ± 0.7 | 91.8 ± 1.6 |
| 100 | 85.7 ± 1.8** | 0.0 ± 0.0*** | 12.1 ± 4.9*** | 0.0 ± 0.0*** |
| 50 | — | 39.4 ± 8.7*** | 46.2 ± 6.9*** | 0.0 ± 0.0*** |
| 20 | — | 74.6 ± 3.2* | 76.2 ± 5.2** | 76.3 ± 4.6* |
| 10 | — | 77.8 ± 2.7 | 80.5 ± 2.7** | 85.9 ± 1.8* |
| 5 | — | 77.7 ± 2.7 | 80.9 ± 3.5* | — |

1. % Aggregation (Mean ± S.E. (n)) n = 3
2. Thrombin: 0.1 u/ml, AA: 100 μM, collagan: 100 μg/ml, PAF: 2 ng/ml
3. *p < 0.05; p < 0.01; *p < 0.001

TABLE 5

Abruquinone F (V) Aggregation %

| (μg/ml) | thrombin | AA | collagen | PAF |
|---|---|---|---|---|
| control | 92.7 ± 0.7 | 91.7 ± 2.4 | 89.3 ± 1.8 | 88.3 ± 1.3 |
| 100 | 40.4 ± 5.0*** | 19.9 ± 82 | 23.7 ± 8.9 | 21.9 ± 10.9*** |

1. % Aggregation (Mean ± S.E. (n)) n = 3
2. Thrombin: 0.1 u/ml, AA: 100 μM, collagan: 100 μg/ml, PAF: 2 ng/ml
3. *p < 0.05; p < 0.01; *p < 0.001

(2) Antiinflammatory activity

The antiinflammatory activity of the present invention was evaluated with the release reaction of neutrophils.

A. The method reported by Barrett, A. J. ("A Laboratory Handbook," edited by Dingle, J. T. PP. 118, 1972) was used to determine the B-glucuronidase concentration in the upper layer, in which a spectrophotometer was used. The neutrophil leukocyte suspension was added into FMLP, mixed, and centrifuged. The upper layer containing the B-glucuronidase was separated and determined by spectrophotometry.

B. The method reported by Absolom, D. R. (Methods Enzymol. 132, 95, 1986) was used to determine the presence of lysozyme. The neutrophil suspension was centrifuged after complete reaction with FMLP. The upper layer added to the substrate of *Micrococcus lysodcikticus* cell was determined by spectrophotometry at a λ of 450 nm.

Tab. 6 shows that compounds I–V at the concentration of 3 μg/ml inhibit perfectly the release of B-glucuronidase and lysozyme from neutrophils.

TABLE 6

| compound (μg/ml) | β-gucuronidase | Percent (% inh) | lysozyme | Release (% inh) | N |
|---|---|---|---|---|---|
| control | 36.8 ± 1.4 | — | 51.3 ± 3.6 | — | 3 |
| I (3) | 2.5 ± 0.1** | 93.2 ± 0.6 | −2.6 ± 0.4** | 105.2 ± 0.8 | 3 |
| (1) | 14.2 ± 1.2** | 61.4 ± 3.3 | 23.6 ± 0.7** | 53.5 ± 3.4 | 3 |
| II (3) | 0.5 ± 0.3** | 98.5 ± 1.0 | −2.2 ± 1.2** | 104.4 ± 2.6 | 3 |
| (1) | 7.0 ± 0.9** | 80.9 ± 2.3 | 22.7 ± 1.9** | 55.5 ± 3.0 | 3 |
| III (3) | 0.9 ± 0.2** | 97.5 ± 0.8 | −3.3 ± 0.9** | 106.7 ± 1.9 | 3 |
| (1) | 6.9 ± 1.5** | 80.8 ± 5.0 | 23.5 ± 4.1** | 54.5 ± 5.9 | 3 |
| IV (3) | 37.4 ± 3.1 | −1.5 ± 5.6 | 50.3 ± 7.2 | 2.4 ± 10.9 | 3 |
| (1) | 31.9 ± 0.7 | 13.1 ± 1.5 | 43.8 ± 2.9 | 14.6 ± 0.5 | 3 |
| V (3) | 2.3 ± 0.8**. | 93.5 ± 2.5 | −4.1 ± 2.8** | 108.4 ± 5.8 | 3 |
| (1) | 8.4 ± 1.8** | 77.5 ± 4.2 | 23.6 ± 3.7** | 54.6 ± 3.7 | 3 |

**p < 0.01

C. The method reported by Markert, M. (Methods Enzymol. 105, 358, 1984) was used to determine the superoxide dimutase. The neutrophil suspension, after induced with FMLP, in the presence of cytochrome C was determined at a λ of 550 nm. The release of superoxide dimutase from neutrophil was obtained.

Tab. 7 shows that compounds I–V at the concentration of 1 μg/ml inhibit perfectly the release of superoxide dimutase from neutrophils induced by FMLP.

TABLE 7

| compound (μg/ml) | Superoxide formation | | |
|---|---|---|---|
| | n mole/$10^6$ cell | % ing | N |
| control | 3.5 ± 0.3 | — | |
| I (0.3) | 1.6 ± 0.2** | 53.7 ± 2.5 | 4 |
| (1) | 0.4 ± 0.1** | 86.3 ± 2.9 | 4 |
| II (0.3) | 0.8 ± 0.1** | 74.8 ± 1.2 | 4 |
| (1) | 0.2 ± 0.1** | 92.9 ± 3.3 | 4 |
| III (0.3) | 0.8 ± 0.1** | 74.3 ± 3.1 | 4 |
| (1) | 0.4 ± 0.1** | 86.0 ± 2.5 | 4 |
| IV (0.3) | 3.2 ± 0.3 | 9.2 ± 4.5 | 4 |
| (1) | 2.8 ± 0.4 | 22.3 ± 3.6 | 4 |
| V (0.3) | 1.1 ± 0.2** | 67.8 ± 7.3 | 4 |
| (1) | 0.3 ± 0.1** | 91.7 ± 2.4 | 4 |

*p < 0.05;
**p < 0.01

(3) Antiallergic evaluation

A. The method reported by Hakanson, R. (Analyt. Biochem. 60, 560, 1972) was used to determine the release of histamine from mast cells, in which the mast cell suspension, after a completed reaction with compound 48/80, was centrifuged. Histamine in the upper layer, after treating with O-phthaldehyde, was determined by the spectophotofluorometry.

B. The method reported by Barrett, A. J. ("A Laboratory Handbook," edited by Dingle, J. T. PP. 118, 1972) was used to determine the release of β-glucuronidase from mast cells. When mast cell suspension was completely reacted with compound 48/80 and then centrifuged. In the upper layer, the substrate of phph-glucuronide was added to determine the β-glucuronidase concentration.

Tab. 8 shows that compounds I–V, at the concentration of 3 μg/ml, inhibited perfectly the release of histamine and β-glucuronidase from mast cells induced by compound 48/80.

The inhibitive activity of the Abruquinone derivatives were found more potent than indomethacin or cromolyn sodium.

TABLE 8

| compound (μg/ml) | β-glucuronidase | Percent (% inh) | N | histamine | Release (% inh) | N |
|---|---|---|---|---|---|---|
| Control | 28.4 ± 1.5 | — | 5 | 35.8 ± 2.5 | — | 3 |
| I (3) | 10.9 ± 2.7** | 59.2 ± 11.7 | 5 | 2.6 ± 0.4** | 105.2 ± 0.8 | 3 |
| (1) | 13.7 ± 3.4** | 50.1 ± 12.3 | 5 | 18.5 ± 3.8** | 49.3 ± 7.6 | 3 |
| II (3) | 15.5 ± 3.4** | 50.3 ± 13.4 | 5 | 14.7 ± 3.5** | 59.7 ± 7.3 | 3 |
| (1) | 13.8 ± 2.3** | 49.6 ± 9.3 | 5 | 21.7 ± 2.6** | 38.2 ± 9.6 | 3 |
| III (3) | 15.1 ± 2.7** | 44.4 ± 11.2 | 5 | 5.6 ± 1.6** | 84.1 ± 4.8 | 3 |
| (1) | 17.5 ± 4.0** | 35.1 ± 16.4 | 5 | 17.8 ± 1.5** | 50.4 ± 1.1 | 3 |
| IV (3) | 25.5 ± 1.3 | 9.3 ± 4.1 | 5 | 29.6 ± 6.0 | 18.1 ± 12.8 | 3 |
| (1) | 24.6 ± 2.7 | 13.6 ± 6.4 | 5 | 25.0 ± 6.0 | 30.6 ± 15.0 | 3 |
| V (3) | 15.0 ± 2.8** | 45.0 ± 11.2 | 5 | 17.4 ± 3.2** | 51.7 ± 7.6 | 3 |

TABLE 8-continued

| compound $\beta$-glucu- ronidase ($\mu$g/ml) | Percent (% inh) | N | Release histamine (% inh) | N |
|---|---|---|---|---|
| (1) 15.1 ± 3.7** | 46.2 ± 12.8 | 5 | 25.3 ± 5.8** 29.6 ± 14.4 | 3 |

**p < 0.01

III. Pharmaceutical compositions

The novel Abruquinone derivatives of this invention, together with a conventional adjuvant, carrier, or diluent, and if desired in the form of pharmaceutically acceptable salts, may be prepared in the form of pharmaceutical compositions and unit dosages. In such forms, they may be employed as solids or liquids for oral use; in the form of suppositories for rectal administration; or in the form of sterile injectable solutions for parental (including subcutaneous) use.

The solid pharmaceutical dosages may comprise disintegrating agents such as starch, sodium carboxymethylcellulose, and/or binders such as ethyl alcohol, glycerin, and/or carriers such as magnesium stearate, lactose, which are prepared by conventional pharmaceutical methods. The preparation of sterile injectable solution dosages, or other liquids, can be adjusted with buffers, such as phosphate solutions, if desired, with auxiliary agents, emulsifiers, which are particularly comprised of aqueous solutions or salt solutions of the novel compounds. The novel pharmaceutical compositions and unit dosages thereof allow the formation of a pharmaceutically acceptable salt, and are extremely useful in the antiplatelet, antiinflammatory, and antiallergic activities. The novel compounds of the present invention may be accordingly administered to a subject, e.g. a living animal body, including a human being, and should be adjusted accordingly to the complexity of the symptoms.

EXAMPLE 1

Isolation of Abruquinone A (I)

An amount of 5 Kg of the roots of the *Abrus precatorius* L. was extracted 5 times with methanol. The solvent of the combined extract was evaporated under reduced pressure, to give 420 g of a red-brown sticky residue. A portion of 320 g of this residue was suspended in water, then extracted 15 times with 500 ml chloroform. The combined extract was then evaporated to give 125 g of Fr. A, which was then subjected to column chromatography through 70–230 mesh silica gel and eluted gradiently with chloroform, ethyl acetate, and methanol. The fractional forms A–I through A–V were collected according to the polarity of the eluents.

The fraction A–II was subjected to silica gel chromatography and eluted gradiently again with chloroform, ethyl acetate, and methanol. Fractions A-II-1–A-II-5 were collected. The fraction A-II-2 was further purified by supelcosil PLC-18 column chromatography to give compound I, which exhibits the form as orange crystals (1.0 gm), after recrystallization with methanol.

The properties of Abruquinone A are analyzed as follows:
mp: 109°–111° C.
EtOH:
UV $\lambda_{max}$ nm (log $\epsilon$):269 (4.03), 398 (2.94)
MS (m/z, %): 360 (M$^+$, 100), 345 (63), 194 (25), 167 (55)
Anal. Calcd. for $C_{19}H_{20}O_7$: C, 63.33; H, 5.59 Found: C, 63.51; H, 5.32
KBr
IR ($\lambda_{max}$ cm$^{-1}$): 1653, 1604, 1517, 1220, 1195, 1127 cm$^{-1}$
$^{13}$C-NMR (CDCl$_3$, $\delta$):
28.96, 30.74, 55.84, 56.38, 61.17, 61.29, 67.97, 100.87, 110.35, 112.09, 130.99, 143.71, 144.69, 145.13, 146.72, 147.88, 148.76, 183.59, 184.14
$^1$H-NMR (CDCl$_3$, $\delta$):
2.71 (1H, dd, J=16.4, 6.0 Hz, H$_{ax}$-4),
3.03 (1H, dd, J=16.4, 6.0 Hz, H$_{eq}$-4),
3.49 (1H, m, H$_{eq}$-3),
3.83 (6H, s, OMe),
4.02 (6H, s, OMe),
4.05 (1H, ddd, J=10.6, 5.7, 1.2 Hz, H$_{ax}$-2),
4.22 (1H, ddd, J=10.6, 3.0, 0.9 Hz, H$_{eq}$-2),
6.38 (1H, d, J=1.2 Hz, H-5'),
6.39 (1H, s, H-8),
6.53 (1H, s, H-5)

EXAMPLE 2

Isolation of Abruquinone B (II)

According to the procedure described in Example 1, 1.8 gm of compound II was obtained from fraction A-II-2 as a red-brown sticky liquid.

The properties of Abruquinone B are analyzed as follows:
EtOH:
UV $\lambda_{max}$ nm (log $\epsilon$) : 268 (4.09), 397 (3.04)
MS (m/z, %): 390 (M$^+$, 100), 375 (55), 197 (94), 194 (36)
Anal. Calcd. for $C_{20}H_{22}O_8$: C, 61.53; H, 5.68 Found: C, 61.35; H, 5.90
KBr
IR ($\lambda_{max}$ cm$^{-1}$): 1654, 1604, 1491, 1130 cm$^{-1}$ (C-0)
$^{13}$C-NMR (CDCl$_3$, $\delta$):
$^1$H-NMR (CDCl$_3$, $\delta$):
29.35 30.81 56.36 61.06 67.98 107.14
114.87 130.86 141.75 141.84 142.30 144.69
145.13 146.40 147.39 183.32 183.82
2.67 (1H, dd, J=16.45, 6.5 Hz, H$_{ax}$-4),
3.01 (1H, dd, J=16.45, 6.5 Hz, H$_{eq}$-4),
3.40 (1H, m, H$_{eq}$-3),
3.75 (3H, s, OMe of C-6),
3.83 (6H, s, OMe of C-7 and C-8),
3.97 (6H, s, OMe of C-2' and C-3'),
4.04 (1H, dd, J=10.86, 1 Hz, H$_{ax}$-2),
4.24 (1H, dd, J=10.71, 1 Hz, H$_{eq}$-2),
6.29 (1H, d, H-5'),
6.30 (1H, s, H-5)

EXAMPLE 3

Isolation of Abruquinone D (III)

According to the procedure described in Example 1, 1.2 gm of compound III was obtained from fraction A-II-3 as a red-brown sticky liquid.

The properties of Abruquinone D are analyzed as follows:
EtOH:
Uv $\lambda_{max}$ nm (log $\epsilon$): 268 (4.01), 392 (2.96)
MS (m/z, %): 376 (M$^+$, 95), 194 (80), 183 (100)
Anal. Calcd. for $C_{19}H_{20}O_8$: C, 60.63; H, 5.36 Found: C, 60.90; H, 5.31
KBr
IR ($\lambda_{max}$ cm$^{-1}$): 3452, 1652, 1504, 1486, 1130 cm$^{-1}$ (C-0)
$^{13}$C-NMR (CDCl$_3$, $\delta$):

29.08 30.76 56.44 60.88 61.13 61.23 67.98
106.36 110.45 130.90 135.64 137.84 141.49 141.79
144.58 145.05 146.41 183.39 183.89
$^1$H-NMR (CDCl$_3$, δ):
2.67 (1H, dd, J=16.2, 6.2 Hz, H$_{ax}$-4),
3.01 (1H, dd, J=16.2, 6.2 Hz, H$_{eq}$-4),
3.42 (1H, m, H$_{eq}$-3),
3.81 (3H, s, OMe of C-6),
3.87 (6H, s, OMe of C-8),
3.99, 4.00 (2X3H, s, OMe of C-2' and C-3'),
4.08 (1H, dd, J=10.8, 0.8 Hz, H$_{ax}$-2),
4.24 (1H, dd, J=10.0, 0.75 Hz, H$_{eq}$-2),
5.51 (1H, s, OH),
6.30 (1H, s, H-5),
6.33 (1H, d, J=1.17 Hz, H-5')

EXAMPLE 4

Isolation of Abruquinone E (IV)

According to the procedure described in Example 1, 0.2 gm of compound IV was obtained from fraction A-II-2 as a red-brown sticky liquid.

The properties of Abruquinone E are analyzed as follows:
EtOH:
UV λ$_{max}$ nm (log ε): 291 (4.21), 392 (2.74)
MS (m/z, %): 420 (M$^+$, 74), 1405 (34), 224 (100), 197 (59)
Anal. Calcd. for C$_{21}$H$_{24}$O$_9$: C, 59.99; H, 5.75 Found: C, 60.15; H, 5.63
KBr
IR(λ$_{max}$ cm$^{-1}$): 1659, 1607, 1491, 1279, 1096 cm$^{-1}$ (C-0)
$^{13}$C-NMR (CDCl$_3$, δ):
29.50 30.92 56.48 61.12 61.50 67.60
107.39 116.69 128.12 141.60 142.23 142.37
142.61 144.35 146.96 155.35 180.09 183.33
$^1$H-NMR (CDCl$_3$, δ):
2.61 (1H, ddd, J=16.23, 5.22, 2.04 Hz, H$_{ax}$-4),
3.11 (IH, dd, J=15.63, 11.94Hz, H$_{eq}$-4),
3.55 (1H, m, H$_{eq}$-3),
3.76 (3H, s, OMe of C-6),
3.85, 3.88 (6H, s, OMe of C-7 and C-8, OMe),
3.96 (6H, s, OMe of C-2' and C-5'),
4.01 (3H, s, OMe of C-3'),
4.16 (1H, ddd, J=10.2, 3.33, 2.13 Hz, H$_{ax}$-2),
4.34 (1H, t, dd, J=10.5 Hz, K$_{eq}$-2),
6.29 (1H, s, H-5)

EXAMPLE 5

Isolation of Abruguinone F (V)

According to the procedure described in Example 1, 0.4 gm of compound V was obtained from fraction A-II-3, as red-brown scales after recrystallization from methanol at −20 C.

The properties of Abruquinone F are analyzed as follows:
mp: 141°–143° C.
EtOH:
UV λ$_{max}$ nm (log ε):268 (4.14), 396 (3.05)
MS (m/z, %): 376 (M$^+$, 27), 195 (100), 194 (22), 183 (19)
Anal. Calcd. for C$_{19}$H$_{20}$O$_8$: C, 60.63; H, 5.36 Found: C, 60.35; H, 5.20

Kbr
IR(λ$_{max}$ cm$^{-1}$):3414, 1651, 1599, 1501, 1126cm$^{-1}$
$^{13}$C-NMR (CDCl$_3$, δ):
29.07 30.98 56.19 60.89 61.06 61.17 68.14
102.94 114.69 130.99 135.34 136.36 138.25 144.71
145.17 146.31 147.07 183.35 183.86
$^1$H-NMR (CDCl$_3$, δ):
2.68 (1H, dd, J=16.4, 6.0 Hz, H$_{ax}$-4),
3.02 (1H, dd, J=16.4, 6.0 Hz, H$_{eq}$-4),
3.43 (1H, m, H$_{eq}$-3),
3.78 (3H, s, OMe of C-6),
3.87 (3H, s, OMe of C-7),
3.99 (6H, s, Ome of C-2' and C-3'),
4.08 (1H, ddd, J=10.7, 6.1 Hz, H$_{ax}$-2),
4.24 (1H, ddd, J=10.7, 3.0, 0.8 Hz, H$_{eq}$-2),
5.54 (1H, s, OH),
6.12 (1H, s, H-5),
6.32 (1H, d, J=1.2, Hz, H-5')

We claim:

1. A method to provide antiinflammatory activity in a subject in need thereof, comprising the step of administering an effective amount of at least one compound selected from the group consisting of Abruquinones A, B, D, E and F, and at least one pharmaceutically acceptable vehicle.

2. A method to inhibit allergic reaction in a subject in need thereof, comprising the step of administering an effective amount of at least one compound selected from the group consisting of Abruquinones A, B, D, E and F, and at least one pharmaceutically acceptable vehicle.

3. The method to provide antiinflammatory activity in accordance to claim 1, wherein said compound is Abruquinone A, which is represented by the following formula:

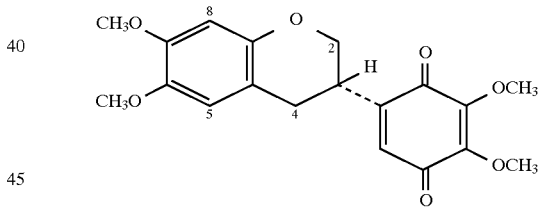

Abruquinone A (Formula I)

4. The method to provide antiinflammatorv activity in accordance to claim 1, wherein said compound is Abruquinone B, which is represented by the following formula:

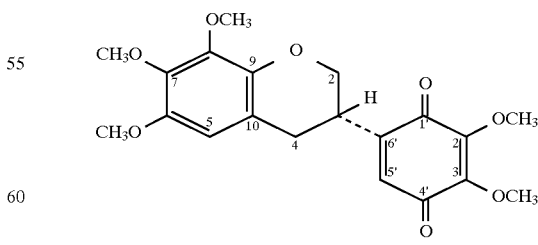

Abruquinone B (Formula II)

5. The method to provide antiinflammatory activity in accordance to claim 1, wherein said compound is Abruquinone D, which is represented by the following formula:

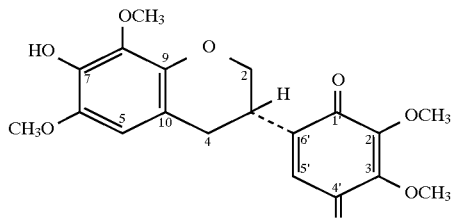

Abruquinone D (Formula III)

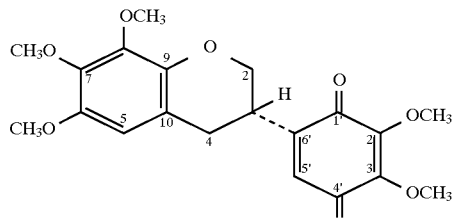

Abruquinone B (Formula II)

6. The method to provide antiinflammatory activity in accordance to claim 1, wherein said compound is Abruquinone E, which is represented by the following formula:

10. The method to inhibit allergic reaction in accordance to claim 2, wherein said compound is Abruquinone D, which is represented by the following formula:

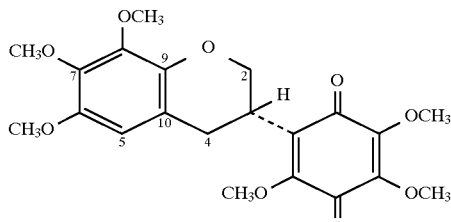

Abruquinone E (Formula IV)

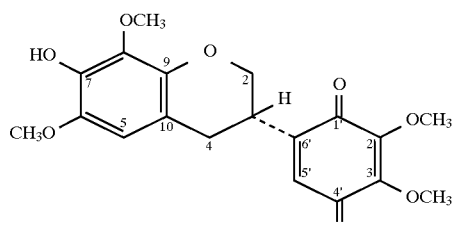

Abruquinone D (Formula III)

7. The method to provide antiinflammatory activity in accordance to claim 1, wherein said compound is Abruquinone F, which is represented by the following formula:

11. The method to inhibit allergic reaction in accordance to claim 2, wherein said compound is Abruquinone E, which is represented by the following formula:

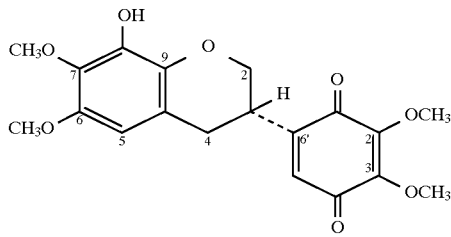

Abruquinone F (Formula V)

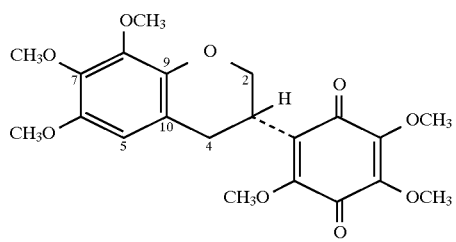

Abruquinone E (Formula IV)

8. The method to inhibit allergic reaction in accordance to claim 2, wherein said compound is Abruquinone A, which is represented by the following formula:

12. The method to inhibit allergic reaction in accordance to claim 2, wherein said compound is Abruquinone F, which is represented by the following formula:

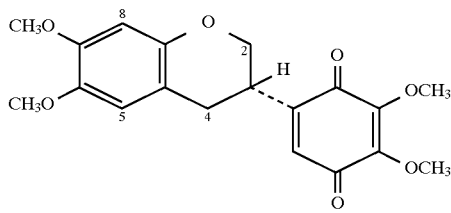

Abruquinone A (Formula I)

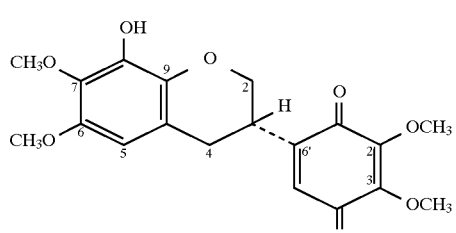

Abruquinone F (Formula V)

9. The method to inhibit allergic reaction in accordance to claim 2, wherein said compound is Abruquinone B, which is represented by the following formula:

* * * * *